US007705148B2

(12) United States Patent
Schils et al.

(10) Patent No.: US 7,705,148 B2
(45) Date of Patent: *Apr. 27, 2010

(54) PROCESSES FOR THE PREPARATION OF 4-[[4-[[4-(2-CYANOETHENYL)-2,6-DIMETHYLPHENYL]AMINO]-2-PYRIMIDINYL]AMINO]BENZONITRILE

(75) Inventors: Didier Philippe Robert Schils, Loupoigne (BE); Joannes Josephus Maria Willems, Oud-Turnhout (BE); Bart Petrus Anna Maria Jozef Medaer, Lille (BE); Elisabeth Therese Jeanne Pasquier, Le Neubourg (FR); Paul Adriaan Jan Janssen, Vosselaar (BE); Jan Heeres, Vosselaar (BE); Ruben Gerardus George Leenders, Nijmegen (NL); Jérôme Emile Georges Guillemont, Ande (FR)

(73) Assignee: Janssen Pharmaceutica N.V. (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/031,011

(22) Filed: Feb. 14, 2008

(65) Prior Publication Data

US 2008/0167464 A1  Jul. 10, 2008

(51) Int. Cl.
C07D 239/48 (2006.01)
C07C 255/42 (2006.01)
C07C 253/30 (2006.01)
C07C 253/20 (2006.01)
A61K 31/505 (2006.01)
A61P 31/18 (2006.01)

(52) U.S. Cl. ........................ 544/323; 544/330; 514/275
(58) Field of Classification Search ................. 544/323, 544/330
See application file for complete search history.

(56) References Cited

U.S. PATENT DOCUMENTS

| 3,459,731 | A | 8/1969 | Gramera et al. |
| 5,691,364 | A | 11/1997 | Buckman et al. |
| 5,958,935 | A | 9/1999 | Davis et al. |
| 6,197,779 | B1 | 3/2001 | Andries et al. |
| 6,838,464 | B2 | 1/2005 | Pease et al. |
| 6,949,544 | B2 | 9/2005 | Bethiel et al. |
| 6,982,091 | B2 | 1/2006 | Pauletti et al. |
| 7,060,827 | B2 | 6/2006 | Singh et al. |
| 7,125,879 | B2 * | 10/2006 | Guillemont et al. ......... 514/256 |
| 7,399,856 | B2 * | 7/2008 | Schils et al. ................ 544/323 |
| 2006/0034797 | A1 | 2/2006 | Arien et al. |
| 2009/0148531 | A1 | 6/2009 | Hantke et al. |

FOREIGN PATENT DOCUMENTS

| CA | 2324919 | 10/1999 |
| DE | 19945982 A1 | 9/1999 |
| EP | 0002341 B1 | 1/1982 |
| EP | 1002795 A1 | 5/1999 |

(Continued)

OTHER PUBLICATIONS

International Search Report dated Nov. 6, 2003 for corresponding Appl. No. PCT/EP03/50366.
International Preliminary Examination Report dated Nov. 30, 2004 for corresponding Appl. No. PCT/EP03/50366.
D'Auria, M., et al. "Photochemical Dimerization in Solution of Arylacrylonitrile Derivatives", Tetrahedron, vol. 53, No. 51, pp. 17307-17316 (1997).

(Continued)

Primary Examiner—Venkataraman Balasubramanian

(57) ABSTRACT

Processes for the preparation of 4-[[4-[[4-(2-cyanoethenyl)-2,6-dimethylphenyl]-amino]-2-pyrimidinyl]amino]benzonitrile of formula (I), a N-oxide, a pharmaceutically acceptable acid addition salt, a quaternary amine or a stereochemically isomeric form thereof are provided, said processes comprise:
a) reacting 4-(2-cyanoethenyl)-2,6-dimethylbenzenamine with an intermediate of formula (III)

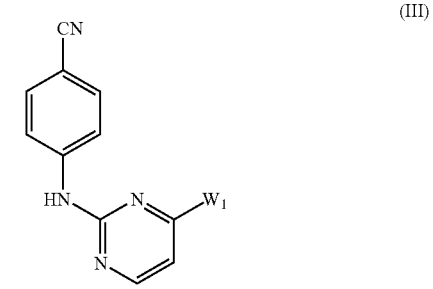

(III)

in the presence of a suitable solvent;
b) reacting an intermediate of formula (IV)

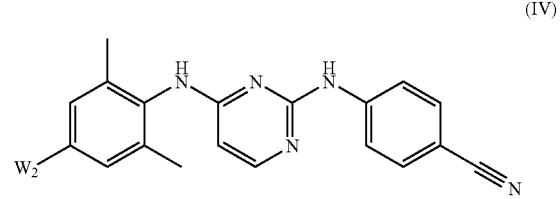

(IV)

with acrylonitrile in the presence of a suitable palladium catalyst, a suitable base and a suitable solvent;
c) dehydrating the corresponding amide of the compound of formula (I).

9 Claims, No Drawings

FOREIGN PATENT DOCUMENTS

| | | |
|---|---|---|
| EP | 0945443 A1 | 9/1999 |
| JP | 2000-35628 A | 2/2000 |
| WO | 97/18839 A1 | 5/1997 |
| WO | 97/19065 A1 | 5/1997 |
| WO | 98/41512 A1 | 9/1998 |
| WO | 99/50250 | 10/1999 |
| WO | 99/50250 A1 | 10/1999 |
| WO | 00/12485 A1 | 3/2000 |
| WO | 00/27825 A1 | 5/2000 |
| WO | 00/53610 | 9/2000 |
| WO | 00/62778 A1 | 10/2000 |
| WO | 00/78731 A1 | 12/2000 |
| WO | 01/22938 A1 | 4/2001 |
| WO | 01/23362 A2 | 4/2001 |
| WO | 01/60816 A1 | 8/2001 |
| WO | 01/64654 A1 | 9/2001 |
| WO | 01/85700 A | 11/2001 |
| WO | 02/08226 A2 | 1/2002 |
| WO | 02/70470 A2 | 9/2002 |
| WO | 03/16306 A1 | 2/2003 |
| WO | 2004/16581 A1 | 2/2004 |
| WO | 2004/50058 A2 | 6/2004 |
| WO | 2005/21001 A1 | 3/2005 |

OTHER PUBLICATIONS

Denton, et al. "Antiretroviral Pre-Exposure Prophylaxis Prevents Vaginal Transmission of HIV-1 in Humanized BLT Mice", PLoS Medicine (Jan. 14, 2008).

Gilead Press Release XP-002314669.

Koyanagi, Y., et al. "Selective Cytotoxicity of Aids Virus Infection Towards HTLV1-Transformed Cell Lines", Int. J. Cancer: 36, pp. 445-451 (1985).

Larock, R. C. "Interconversion of Nitriles, Carboxylic Acids and Derivatives", John Wiley & Sons, Inc. (199) pp. 1983-1985.

Ludovici, D., et al. "Evolution of Anti-Hiv Drug Candidates. Part 3: Diarylpyrimidine (DAPY) Analogues", Bioorganic & Medicinal Chemistry Letters, vol. 11 pp. 2235-2239 (2001).

Mayo Clinic, HIV Infection Symptoms According to Infection Stage, vvww.mayoclinic.com/health/hiv-aids/DS00005/DSECTION-symptoms (Nov. 2, 2009).

Miles, K., "The Growing HIV Pandemic", HIV Diagnoses: Community Practitioner (2005) vol. 78, No. 8 pp. 292-294.

Pavia, A., "Abacavir/Lamiviudne in Connection With Efavirenz, Amprenavir/Ritonavir or Stavudine", XP 002274550, The XIV International AIDS Conference.

Squires, K., "An Introduction to Nucleoside and Nucleotide Analogues", Antiviral Therapy, 6 Suppl.3, XP 009042950 pp. 1-14.

Supuran, CI., et al. "Carbonic Anhyddrase Inhibitors: Synthesis of Sulfonamides Incorporating 2,4,6-Trisubstituted-Pyridinium-Ethylcarboxamido Moieties Possessing Membrane-Impermeability and in Vivo Selectively for the Membrane-Bound (CA IV) Versus the Cytosolic (CA 1 and CA II) Isozymes", Journal of Enzyme Inhibitor and Medicinal Chemistry vol. 15, pp. 381-340 (2000).

Young, B., "Can Abacavir Be Given Once-A-Day?" the 43rd Interscience Conference on Antimicrobial Agents and Chemotherapy XP-002274551.

International Search report, mailing date Nov. 26, 2002, for corresponding Application No. PCT/EP2002/08953.

International Search Report, mailing date Feb. 7, 2005, for corresponding Application No. PCT/EP2004/052028 (related by subject matter).

Canadian Search Report dated Feb. 19, 2007 for corresponding Application No. CA 2,452,217.

* cited by examiner

PROCESSES FOR THE PREPARATION OF 4-[[4-[[4-(2-CYANOETHENYL)-2,6-DIMETHYLPHENYL]AMINO]-2-PYRIMIDINYL]AMINO]BENZONITRILE

CROSS REFERENCE TO RELATED APPLICATIONS

This application claims priority to U.S. application Ser. No. 10/523,753 filed Feb. 8, 2005 (now U.S. Pat. No. 7,399,856), which is the national stage of application no. PCT/EP2003/050366 filed Aug. 7, 2003, which application claims priority from EP patent application no. 02078306.4 filed Aug. 9, 2002.

The present invention relates to 4-[[4-[[4-(2-cyanoethenyl)-2,6-dimethylphenyl]-amino]-2-pyrimidinyl]amino] benzonitrile, a N-oxide, a pharmaceutically acceptable addition salt, a quaternary amine or a stereochemically isomeric form thereof and to the preparation thereof as well as to the preparation of a key intermediate in said preparation.

WO 99/50250 discloses substituted diaminopyrimidine compounds having HIV (Human Immunodeficiency Virus) inhibiting properties and the preparation thereof. WO 03/16306 discloses the preparation of 4-[[4-[[4-(2-cyanoethenyl)-2,6-dimethylphenyl]amino]-2-pyrimidinyl]amino] benzonitrile from a melt of [4-[(4-chloro-2-pyrimidinyl) amino]benzonitrile and 3-(4-amino-3,5-dimethylphenyl)-2-propenenitrile.

4-[[4-[[4-(2-cyanoethenyl)-2,6-dimethylphenyl]amino]-2-pyrimidinyl]amino]-benzonitrile, N-oxides, pharmaceutically acceptable addition salts, quaternary amines and stereochemically isomeric forms thereof are novel, very potent HIV, especially HIV-1, replication inhibiting compounds. They have a high ability to inhibit the replication of the wild type Human Immunodeficiency Virus as well as resistant mutant strains thereof.

Therefore, 4-[[4-[[4-(2-cyanoethenyl)-2,6-dimethylphenyl]amino]-2-pyrimidinyl]-amino]benzonitrile, N-oxides, pharmaceutically acceptable addition salts, quaternary amines and stereochemically isomeric forms thereof can be used as a medicine. They may be useful in the prevention or treatment of HIV infection, including the prevention or the treatment of HIV infection of mutant strains, i.e. strains which have become resistant to art-known drug(s) (drug or multidrug resistant HIV strains); they may be useful in the treatment of warm-blooded animals including humans infected with HIV or infected with viruses whose existence is mediated by, or depends upon, the enzyme reverse transcriptase, or for the prophylaxis of those infections in these warm-blooded animals. Thus, the present invention also relates to the use of 4-[[4-[[4-(2-cyanoethenyl)-2,6-dimethylphenyl]amino]-2-pyrimidinyl]amino]benzonitrile, a N-oxide, a pharmaceutically acceptable addition salt, a quaternary amine or a stereochemically isomeric form thereof for the manufacture of a medicament for the prevention or the treatment of HIV infection. The invention also relates to a method of treating warm-blooded animals, including humans, suffering from or a method of preventing warm-blooded animals, including humans, to suffer from viral infections, especially HIV infections. Said method comprises the administration, preferably oral administration, of an effective amount of a compound of formula (I), a N-oxide form, a pharmaceutically acceptable addition salt, a quaternary amine or a possible stereoisomeric form thereof, to warm-blooded animals, including humans.

The present invention also provides compositions for treating viral infections comprising a therapeutically effective amount of 4-[[4-[[4-(2-cyanoethenyl)-2,6-dimethylphenyl] amino]-2-pyrimidinyl]amino]benzonitrile, a N-oxide, a pharmaceutically acceptable addition salt, a quaternary amine or a stereochemically isomeric form thereof and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

The HIV replication inhibiting activity of 4-[[4-[[4-(2-cyanoethenyl)-2,6-dimethylphenyl]amino]-2-pyrimidinyl] amino]benzonitrile, a N-oxide, a pharmaceutically acceptable addition salt, a quaternary amine or a stereochemically isomeric form thereof, can be tested using the following test.

Determination of Anti-HIV Activity

A rapid, sensitive and automated assay procedure was used for the in vitro evaluation of anti-HIV agents. An HIV-1 transformed T4-cell line, MT-4, which was previously shown (Koyanagi et al., *Int. J. Cancer*, 36, 445-451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration ($CC_{50}$ in M) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%,}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in M). The ratio of $CC_{50}$ to $IC_{50}$ was defined as the selectivity index (SI).

The results obtained for Compound X, i.e

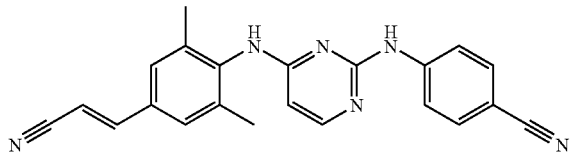

(E-isomer), are the following:
$IC_{50}=10^{-9.4}$M;
$CC_{50}=10^{-5}$ M;
SI of $10^{-5}$ M/$10^{-9.4}$M=25,119.

Compound X was also tested for its replication inhibiting activity towards resistant mutants of HIV-1 (single and double mutants). The obtained results revealed a high activity of Compound X against resistant strains.

In order to ensure an economical supply of the compounds of the invention for development purposes and marketing, an efficient synthetic process which can be carried out on a large, commercial scale is required for the production of the compounds.

It is an object of the present invention to provide processes for the preparation of 4-[[4-[[4-(2-cyanoethenyl)-2,6-dimethylphenyl]amino]-2-pyrimidinyl]amino]benzonitrile, a N-oxide, a pharmaceutically acceptable addition salt, a quaternary amine or a stereochemically isomeric form thereof, with a high yield and under conditions which provide economic advantages for operation on a large, commercial scale.

The present invention therefore provides a process for the preparation of 4-[[4-[[4-(2-cyanoethenyl)-2,6-dimethylphenyl]amino]-2-pyrimidinyl]amino]benzonitrile of formula (I), a N-oxide, a pharmaceutically acceptable addition salt, a quaternary amine or a stereochemically isomeric form thereof,

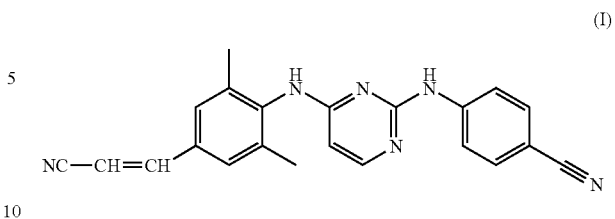

which comprises reacting an intermediate of formula (II), an appropriate acid addition salt or a stereochemically isomeric form thereof

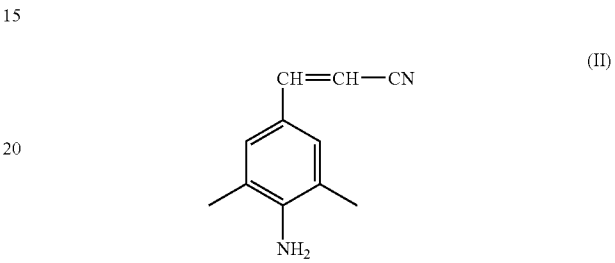

with an intermediate of formula (III), an appropriate acid addition salt or a N-oxide thereof

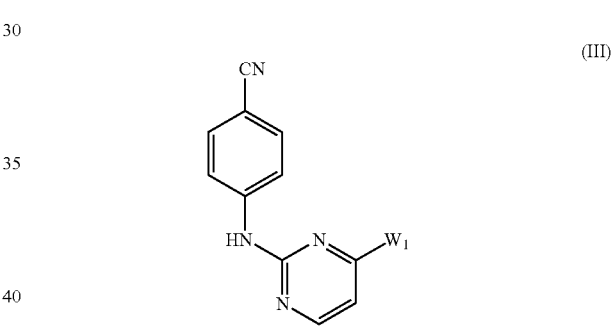

wherein $W_1$ represents a suitable leaving group, in the presence of a suitable solvent.

Suitable leaving groups represented by $W_1$ are for example halo, triflate, tosylate, methylsulfonyl and the like. Preferably, $W_1$ represents halo, more particularly chloro.

Suitable solvents in the above reaction are for example acetonitrile; an alcohol, such as for example ethanol, 2-propanol, 2-propanol-HCl; N,N-dimethylformamide; N,N-dimethylacetamide; 1-methyl-2-pyrrolidinone; 1,4-dioxane; propyleneglycol monomethylether. Preferably the solvent is acetonitrile; an alcohol, such as for example ethanol, 2-propanol, 2-propanol-HCl; N,N-dimethylformamide; N,N-dimethylacetamide; propyleneglycol monomethylether. More preferably, the solvent is 2-propanol, 6 N HCl in 2-propanol or acetonitrile, especially acetonitrile.

Preferably, the intermediate of formula (II) is used as an acid addition salt, especially the hydrochloric acid addition salt, and the intermediate of formula (III) is preferably used as free base.

The product resulting from the above described reaction can conveniently be isolated as a base or as an acid addition salt, and it can further be converted into an acid addition salt by treatment with an acid, or conversely, the acid addition salt form can be converted into the free base by treatment with alkali and, if desired, stereochemically isomeric forms, N-oxide forms or quaternary amines of the product can be formed. The isolation of the reaction product from the reaction medium and, if necessary the further purification, can be performed according to methodologies generally known in the art such as, for example, extraction, crystallization, distillation, trituration and chromatography.

According to another aspect of the present invention, there is provided a process for the preparation of 4-[[4-[[4-(2-cyanoethenyl)-2,6-dimethylphenyl]amino]-2-pyrimidinyl]amino]benzonitrile of formula (I), a N-oxide, a pharmaceutically acceptable acid addition salt, a quaternary amine or a stereochemically isomeric form thereof

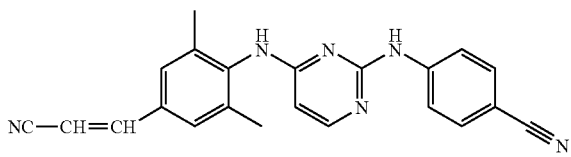

(I)

which comprises reacting an intermediate of formula (IV), an appropriate acid addition salt or a N-oxide thereof

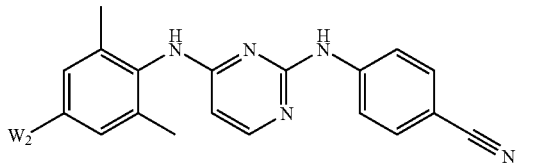

(IV)

wherein $W_2$ represents a suitable leaving group, with acrylonitrile in the presence of a suitable palladium catalyst, a suitable base and a suitable solvent.

Suitable leaving groups represented by $W_2$ are for example halo, triflate, tosylate, mesylate and the like. Preferably, $W_2$ is halo, more particularly iodo or bromo.

The palladium (Pd) catalyst may be a homogeneous Pd catalyst, such as for example Pd(OAc)$_2$, PdCl$_2$, Pd(PPh$_3$)$_4$, Pd(PPh$_3$)$_2$Cl$_2$, Pd$_2$(dba)$_3$ (tris(dibenzylidene acetone)dipalladium), palladium thiomethylphenylglutaramide metallacycle and the like, or a heterogeneous Pd catalyst, such as for example palladium on charcoal, palladium on metal oxides, palladium on zeolites.

Preferably, the palladium catalyst is a heterogeneous Pd catalyst, more preferably palladium on charcoal (Pd/C). Pd/C is a recoverable catalyst, is stable and relatively inexpensive. It can be easily separated (filtration) from the reaction mixture thereby reducing the risk of Pd traces in the final product. The use of Pd/C also avoids the need for ligands, such as for example phosphine ligands, which are expensive, toxic and contaminants of the synthesized products.

Suitable bases are for example sodium acetate, potassium acetate, N,N-diethylethanamine, sodium hydrogencarbonate, sodium hydroxide and the like.

Suitable solvents are for example acetonitrile, N,N-dimethylacetamide, an ionic liquid e.g. [bmim]PF$_6$, N,N-dimethylformamide, water, tetrahydrofuran, dimethylsulphoxide, 1-methyl-2-pyrrolidinone and the like.

The product resulting from the above described reaction can, if desired, be converted into an acid addition salt by treatment with an acid and, if desired, stereochemically isomeric forms, N-oxide forms or quaternary amines of the product can be formed. The isolation of the reaction product from the reaction medium and, if necessary the further purification, can be performed according to methodologies generally known in the art such as, for example, extraction, crystallization, distillation, trituration and chromatography.

Alternatively, the compound of formula (I) can also be prepared by dehydrating the corresponding amide derivative.

Therefore, the present invention also provides a process for the preparation of 4-[[4-[[4-(2-cyanoethenyl)-2,6-dimethylphenyl]amino]-2-pyrimidinyl]amino]benzonitrile of formula (I), a N-oxide, a pharmaceutically acceptable acid addition salt, a quaternary amine or a stereochemically isomeric form thereof,

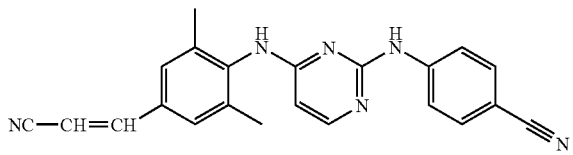

(I)

which comprises reacting an intermediate of formula (VI), an appropriate acid addition salt or a stereochemically isomeric form thereof

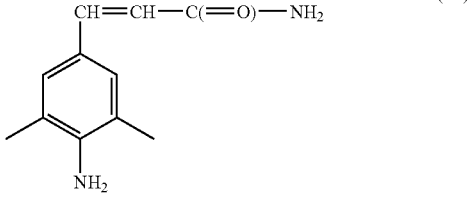

(VI)

with an intermediate of formula (III), an appropriate acid addition salt or a N-oxide thereof

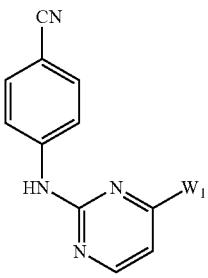

(III)

wherein $W_1$ represents a suitable leaving group, in the presence of a suitable solvent, followed by dehydration of the thus obtained intermediate of formula (VII), a pharmaceutically acceptable acid addition salt, a stereochemically isomeric form or a N-oxide thereof

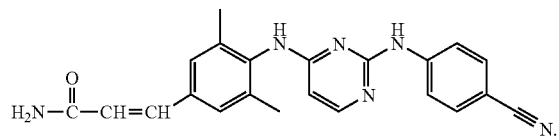

(VII)

Suitable leaving groups represented by $W_1$ are for example halo, triflate, tosylate, methylsulfonyl and the like. Preferably, $W_1$ represents halo, more particularly chloro.

Suitable solvents in the above reaction are for example acetonitrile; an alcohol, such as for example ethanol, 2-propanol, 2-propanol-HCl; N,N-dimethylformamide; N,N-dimethylacetamide; 1-methyl-2-pyrrolidinone; 1,4-dioxane; propyleneglycol monomethylether. Preferably the solvent is acetonitrile; an alcohol, such as for example ethanol, 2-propanol, 2-propanol-HCl; N,N-dimethylformamide; N,N-dimethylacetamide; propyleneglycol monomethylether. More preferably, the solvent is 2-propanol, 6 N HCl in 2-propanol or acetonitrile.

The conversion of the intermediate of formula (VII) into the compound of formula (I), i.e. the dehydration step, can be performed according to methodologies well-known to the person skilled in the art, such as the ones disclosed in "Comprehensive Organic Transformations. A guide to functional group preparations" by Richard C. Larock, John Wiley & Sons, Inc, 1999, p 1983-1985, which is incorporated herein as reference. Different suitable reagents are enumerated in said reference, such as for example $SOCl_2$, $HOSO_2NH_2$, $ClSO_2NCO$, $MeO_2CNSO_2NEt_3$, $PhSO_2Cl$, TsCl, $P_2O_5$, $(Ph_3PO_3SCF_3)O_3SCF_3$, polyphosphate ester, $(EtO)_2POP(OEt)_2$, $(EtO)_3PI_2$, 2-chloro-1,3,2-dioxaphospholane, 2,2,2-trichloro-2,2-dihydro-1,3,2-dioxaphospholane, $POCl_3$, $PPh_3$, $P(NCl_2)_3$, $P(NEt_2)_3$, $COCl_2$, $NaCl \cdot AlCl_3$, ClCOCOCl, $ClCO_2Me$, $Cl_3CCOCl$, $(CF_3CO)_2O$, $Cl_3CN=CCl_2$, 2,4,6-trichloro-1,3,5-triazine, $NaCl \cdot AlCl_3$, $HN(SiMe_2)_3$, $N(SiMe_2)_4$, methane sulfonyl chloride and the like. All the reagents listed in said publication are incorporated herein by reference.

The product resulting from the above described reaction can conveniently be isolated as a base or as an acid addition salt, and it can further be converted into an acid addition salt by treatment with an acid, or conversely, the acid addition salt form can be converted into the free base by treatment with alkali and, if desired, stereochemically isomeric forms, N-oxide forms or quaternary amines of the product can be formed. The isolation of the reaction product from the reaction medium and, if necessary the further purification, can be performed according to methodologies generally known in the art such as, for example, extraction, crystallization, distillation, trituration and chromatography.

Further, the present invention also concerns a process for the preparation of 4-[[4-[[4-(2-cyanoethenyl)-2,6-dimethylphenyl]amino]-2-pyrimidinyl]amino]benzonitrile of formula (I), a N-oxide, a pharmaceutically acceptable acid addition salt, a quaternary amine or a stereochemically isomeric form thereof

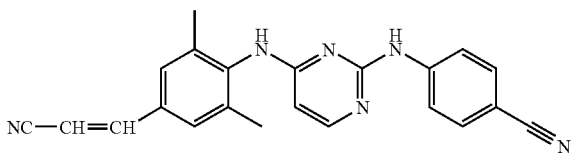

(I)

which comprises reacting an intermediate of formula (IV), an appropriate acid addition salt or N-oxide thereof

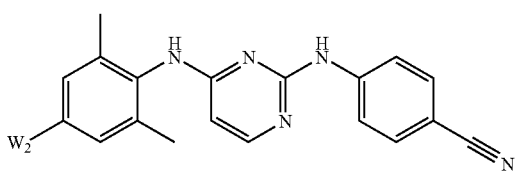

(IV)

wherein $W_2$ represents a suitable leaving group, with acrylamide in the presence of a suitable palladium catalyst, a suitable base and a suitable solvent, followed by dehydration of the thus obtained intermediate of formula (VII), a pharmaceutically acceptable acid addition salt, a stereochemically isomeric form or N-oxide thereof

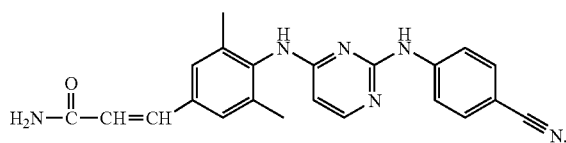

(VII)

Suitable leaving groups represented by $W_2$ are for example halo, triflate, tosylate, mesylate and the like. Preferably, $W_2$ is halo, more particularly iodo or bromo.

The palladium (Pd) catalyst may be a homogeneous Pd catalyst, such as for example $Pd(OAc)_2$, $PdCl_2$, $Pd(PPh_3)_4$, $Pd(PPh_3)_2Cl_2$, $Pd_2(dba)_3$ (tris(dibenzylidene acetone)dipalladium), palladium thiomethylphenylglutaramide metallacycle and the like, or a heterogeneous Pd catalyst, such as for example palladium on charcoal, palladium on metal oxides, palladium on zeolites.

Preferably, the palladium catalyst is a heterogeneous Pd catalyst, more preferably palladium on charcoal (Pd/C). Pd/C is a recoverable catalyst, is stable and relatively inexpensive. It can be easily separated (filtration) from the reaction mixture thereby reducing the risk of Pd traces in the final product. The use of Pd/C also avoids the need for ligands, such as for example phosphine ligands, which are expensive, toxic and contaminants of the synthesized products.

Suitable bases are for example sodium acetate, potassium acetate, N,N-diethylethanamine, sodium hydrogencarbonate, sodium hydroxide and the like.

Suitable solvents are for example acetonitrile, N,N-dimethylacetamide, an ionic liquid e.g. [bmim]$PF_6$, N,N-dimethylformamide, water, tetrahydrofuran, dimethylsulphoxide, 1-methyl-2-pyrrolidinone and the like.

The conversion of the intermediate of formula (VII) into the compound of formula (I), i.e. the dehydration step, can be performed according to methodologies well-known to the person skilled in the art, such as the ones disclosed in "Comprehensive Organic Transformations. A guide to functional group preparations" by Richard C. Larock, John Wiley & Sons, Inc, 1999, p 1983-1985, which is incorporated herein as reference. Different suitable reagents are enumerated in said reference, such as for example $SOCl_2$, $HOSO_2NH_2$, $ClSO_2NCO$, $MeO_2CNSO_2NEt_3$, $PhSO_2Cl$, TsCl, $P_2O_5$, $(Ph_3PO_3SCF_3)O_3SCF_3$, polyphosphate ester, $(EtO)_2POP(OEt)_2$, $(EtO)_3PI_2$, 2-chloro-1,3,2-dioxaphospholane, 2,2,2-trichloro-2,2-dihydro-1,3,2-dioxaphospholane, $POCl_3$, $PPh_3$, $P(NCl_2)_3$, $P(NEt_2)_3$, $COCl_2$, $NaCl.AlCl_3$, ClCOCOCl, $ClCO_2Me$, $Cl_3CCOCl$, $(CF_3CO)_2O$, $Cl_3CN=CCl_2$, 2,4,6-trichloro-1,3,5-triazine, $NaCl.AlCl_3$, $HN(SiMe_2)_3$, $N(SiMe_2)_4$, methane sulfonyl chloride and the like. All the reagents listed in said publication are incorporated herein by reference.

The product resulting from the above described reaction can, if desired, be converted into an acid addition salt by treatment with an acid and, if desired, stereochemically isomeric forms, N-oxide forms or quaternary amines of the product can be formed. The isolation of the reaction product from the reaction medium and, if necessary the further purification, can be performed according to methodologies generally known in the art such as, for example, extraction, crystallization, distillation, trituration and chromatography.

In order to arrive at an efficient synthetic process, it is not sufficient to optimize only the final reaction step, i.e. the reaction step in which the desired product is formed, but the synthesis of the intermediates also needs to be optimized.

Therefore, a further aspect of the present invention relates to the provision of a process for the preparation of a key intermediate, i.e. the intermediate of formula (II), in the synthesis of the compound of formula (I), or a N-oxide, a pharmaceutically acceptable addition salt, a quaternary amine or stereochemically isomeric form thereof.

Thus, the present invention also provides a process for the preparation of an intermediate of formula (II), an appropriate acid addition salt, a quaternary amine or a stereochemically isomeric form thereof

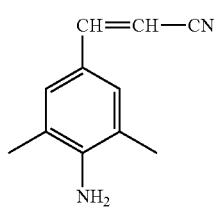
(II)

which comprises reacting an intermediate of formula (V), an appropriate acid addition salt or a quaternary amine thereof

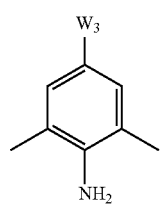
(V)

wherein $W_3$ represents a suitable leaving group, with acrylonitrile in the presence of a suitable palladium catalyst, a suitable base and a suitable solvent.

Suitable leaving groups represented by $W_3$ are for example halo, triflate, tosylate, mesylate and the like. Preferably, $W_3$ is halo, more particularly iodo or bromo. Most preferred is iodo.

The palladium (Pd) catalyst may be a homogeneous Pd catalyst, such as for example $Pd(OAc)_2$, $PdCl_2$, $Pd(PPh_3)_4$, $Pd(PPh_3)_2Cl_2$, $Pd_2(dba)_3$ (tris(dibenzylidene acetone)dipalladium), palladium thiomethylphenylglutaramide metallacycle and the like, or a heterogeneous Pd catalyst, such as for example palladium on charcoal, palladium on metal oxides, palladium on zeolites.

Preferably, the palladium catalyst is a heterogeneous Pd catalyst, more preferably palladium on charcoal (Pd/C). Pd/C is a recoverable catalyst, is stable and relatively inexpensive. It can be easily separated (filtration) from the reaction mixture thereby reducing the risk of Pd traces in the final product. The use of Pd/C also avoids the need for ligands, such as for example phosphine ligands, which are expensive, toxic and contaminants of the synthesized products.

Suitable bases are for example sodium acetate, potassium acetate, N,N-diethylethanamine, sodium hydrogencarbonate, sodium hydroxide and the like.

Suitable solvents are for example acetonitrile, N,N-dimethylacetamide, an ionic liquid e.g. [bmim]$PF_6$, N,N-dimethylformamide, water, tetrahydrofuran, dimethylsulphoxide, 1-methyl-2-pyrrolidinone and the like.

The product resulting from the above described reaction can, if desired, be converted into an acid addition salt by treatment with an acid and, if desired, stereochemically isomeric forms, N-oxide forms or quaternary amines of the product can be formed. The isolation of the reaction product from the reaction medium and, if necessary the further purification, can be performed according to methodologies generally known in the art such as, for example, extraction, crystallization, distillation, trituration and chromatography.

Alternatively, the intermediate of formula (II) can also be prepared by dehydrating the corresponding amide derivative.

Thus, the present invention also relates to a process for the preparation of an intermediate of formula (II), an appropriate acid addition salt, a quaternary amine or a stereochemically isomeric form thereof

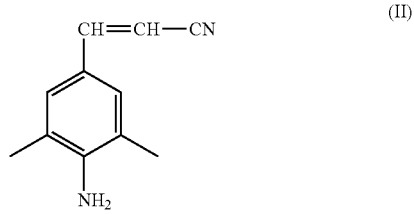
(II)

which comprises reacting an intermediate of formula (V), an appropriate acid addition salt or a quaternary amine thereof

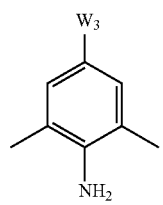

wherein $W_3$ represents a suitable leaving group, with acrylamide in the presence of a suitable palladium catalyst, a suitable base and a suitable solvent, followed by dehydration of the thus obtained intermediate of formula (VI), an appropriate acid addition salt, a quaternary amine or a stereochemically isomeric form thereof

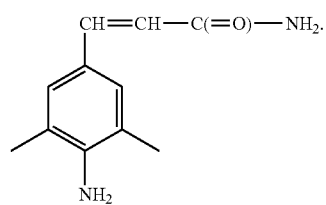

Suitable leaving groups represented by $W_3$ are for example halo, triflate, tosylate, mesylate and the like. Preferably, $W_3$ is halo, more particularly iodo or bromo.

The palladium (Pd) catalyst may be a homogeneous Pd catalyst, such as for example $Pd(OAc)_2$, $PdCl_2$, $Pd(PPh_3)_4$, $Pd(PPh_3)_2Cl_2$, $Pd_2(dba)_3$ (tris(dibenzylidene acetone)dipalladium), palladium thiomethylphenylglutaramide metallacycle and the like, or a heterogeneous Pd catalyst, such as for example palladium on charcoal, palladium on metal oxides, palladium on zeolites.

Preferably, the palladium catalyst is a heterogeneous Pd catalyst, more preferably palladium on charcoal (Pd/C). Pd/C is a recoverable catalyst, is stable and relatively inexpensive. It can be easily separated (filtration) from the reaction mixture thereby reducing the risk of Pd traces in the final product. The use of Pd/C also avoids the need for ligands, such as for example phosphine ligands, which are expensive, toxic and contaminants of the synthesized products.

Suitable bases are for example sodium acetate, potassium acetate, N,N-diethylethanamine, sodium hydrogencarbonate, sodium hydroxide and the like.

Suitable solvents are for example acetonitrile, N,N-dimethylacetamide, an ionic liquid e.g. [bmim]$PF_6$, N,N-dimethylformamide, water, tetrahydrofuran, dimethylsulphoxide, 1-methyl-2-pyrrolidinone and the like.

The conversion of the intermediate of formula (VI) into the intermediate of formula (II), i.e. the dehydration step, can be performed according to methodologies well-known to the person skilled in the art, such as the ones disclosed in "Comprehensive Organic Transformations. A guide to functional group preparations" by Richard C. Larock, John Wiley & Sons, Inc, 1999, p 1983-1985, which is incorporated herein as reference. Different suitable reagents are enumerated in said reference, such as for example $SOCl_2$, $HOSO_2NH_2$, $ClSO_2NCO$, $MeO_2CNSO_2$ $NEt_3$, $PhSO_2Cl$, $TsCl$, $P_2O_5$, $(Ph_3PO_3SCF_3)O_3SCF_3$, polyphosphate ester, $(EtO)_2POP(OEt)_2$, $(EtO)_3PI_2$, 2-chloro-1,3,2-dioxapholane, 2,2,2-trichloro-2,2-dihydro-1,3,2-dioxaphospholane, $POCl_3$, $PPh_3$, $P(NCl_2)_3$, $P(NEt_2)_3$, $COCl_2$, $NaCl.AlCl_3$, $ClCOCOCl$, $ClCO_2Me$, $Cl_3CCOCl$, $(CF_3CO)_2O$, $Cl_3CN=CCl_2$, 2,4,6-trichloro-1,3,5-triazine, $NaCl.AlCl_3$, $HN(SiMe_2)_3$, $N(SiMe_2)_4$, methane sulfonyl chloride and the like. All the reagents listed in said publication are incorporated herein by reference.

The product resulting from the above described reaction can, if desired, be converted into an acid addition salt by treatment with an acid and, if desired, stereochemically isomeric forms, N-oxide forms or quaternary amines of the product can be formed. The isolation of the reaction product from the reaction medium and, if necessary the further purification, can be performed according to methodologies generally known in the art such as, for example, extraction, crystallization, distillation, trituration and chromatography.

As used hereinbefore or hereinafter, the term halo is generic to fluoro, chloro, bromo and iodo.

For therapeutic use, salts of the compound of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove or hereinafter are meant to comprise the therapeutically active non-toxic acid addition salt forms which the compound of formula (I) is able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term addition salt also comprises the hydrates and solvent addition forms which the compound of formula (I) is able to form. Examples of such forms are e.g. hydrates, alcoholates and the like.

The term "quaternary amine" as used hereinbefore or hereinafter defines the quaternary ammonium salts which the compound of formula (I) is able to form by reaction between a basic nitrogen of the compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compound of formula (I) wherein one or several tertiary nitrogen atoms are oxidized to the so-called N-oxide.

The compound of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

It will be appreciated that the compound of formula (I) and the N-oxides, addition salts, quaternary amines and stereochemically isomeric forms thereof may contain one or more centers of chirality and exists as stereochemically isomeric forms.

The term "stereochemically isomeric forms" as used hereinbefore or hereinafter defines all the possible stereoisomeric forms which the compound of formula (I), and the N-oxides, addition salts, quaternary amines or physiologically functional derivatives thereof may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and the N-oxides, salts, solvates or quaternary amines thereof substantially free, i.e. associated with less than 10%, preferably less than 5%, in particular less than 2% and most preferably less than 1% of the other isomers. In particular, stereogenic centers may have the R- or S-configuration or the cis- or trans-configuration; e.g. substituents on bivalent cyclic (partially) saturated radicals may have either the cis- or trans-configuration. The compound of formula (I) can have an E (entgegen) or Z (zusammen)-stereochemistry at the double bond. When the compound of formula (I) is specified as (E), this means that the compound is substantially free of the (Z) isomer. The terms cis, trans, R, S, E and Z are well known to a person skilled in the art. Stereochemically isomeric forms of the compound of formula (I) are obviously intended to be embraced within the scope of this invention.

Whenever used hereinbefore or hereinafter, the term "compound of formula (I)" is meant to also include the N-oxide forms, the addition salts, the quaternary amines and the stereochemically isomeric forms thereof. Of special interest are those compounds of formula (I) which are stereochemically pure. A preferred compound is Compound X.

The Z-isomer of 4-[[4-[[4-(2-cyanoethenyl)-2,6-dimethylphenyl]amino]-2-pyrimidinyl]amino]benzonitrile can also be prepared according to the reactions of the present invention and can be isolated according to art-known methodologies. Hence, 4-[[4-[[4-(2-cyanoethenyl)-2,6-dimethylphenyl]amino]-2-pyrimidinyl]amino]benzonitrile (Z) is also embraced by the present invention.

The following examples illustrate the present invention.

Experimental Part

A. Preparation of the Intermediate Compounds

EXAMPLE A1

Preparation of Intermediate (II)

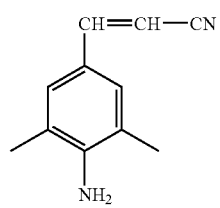

(II)

a) To a solution of 159 g of 4-iodo-2,6-dimethyl-benzenamine in 650 ml of N,N-dimethylacetamide was added 63.8 g of sodium acetate. The reaction mixture was kept under nitrogen atmosphere. 7 g of moistened palladium on charcoal (Pd/C 10%) and 64.4 ml of acrylonitrile was added. The reaction mixture was heated to 130° C. and stirred overnight. After cooling to room temperature, 0.5 l of toluene and 0.5 l of N,N-dimethylacetamide was added. The reaction mixture was filtered over Dicalite and the residue was washed with 0.5 l of toluene. Water (6 l) was added to the mixture which was stirred for 30 minutes. The layers were separated. To the aqueous layer, 1 l of toluene was added and the mixture was stirred for 30 minutes. The layers were separated again. The separated organic layers were collected and the solvent was evaporated. Yield: 123 g of the intermediate of formula (II).

The retention time of intermediate (II) on CPSIL8CB (25 m×0.32 mm×0.5 μm) purged with He with an initial temperature of 40° C. increased with 10° C./minute till a temperature of 300° C., was 17.50 minutes for the (Z) isomer and 18.77 minutes for the (E) isomer.

EXAMPLE A2

Preparation of the Hydrochloric Acid Salt (1:1) of the Intermediate of Formula (II)

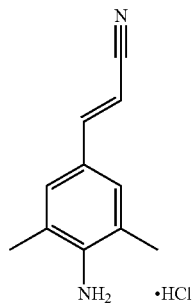

a) To a mixture of 123 g of the intermediate of formula (II) in 630 ml of ethanol was added 1,25 l of diisopropyl ether. The reaction mixture was kept under nitrogen atmosphere. The mixture was heated to 60° C. and stirred for 30 minutes. 120 ml of a 6 N solution of hydrochloric acid in 2-propanol was added and the mixture was stirred for 30 minutes. After cooling to room temperature, the reaction mixture was filtered and the residue was washed with 100 ml of 2-propanol. The resulting residue was dried under reduced pressure at 50° C. Yield: 103 g (77%) of the hydrochloric acid salt (1:1) of the intermediate of formula (II).

b) 1,012 kg of moistened palladium on charcoal (Pd/C 10%), 9,361 kg of sodium acetate and 34,41 kg of N,N-dimethylacetamide were introduced in a reactor and put under nitrogen atmosphere. The mixture was stirred and heated at 140° C. 23,497 kg of 4-iodo-2,6-dimethyl-benzeneamine, 7,569 kg of acrylonitrile and 54,98 kg of N,N-dimethylacetamide were introduced in a second reactor and put under nitrogen atmosphere. The mixture was stirred at room temperature for 30 minutes. The solution of the second reactor was transferred to the first reactor over 1 hour and the temperature of the first reactor was maintained at 140° C. The reaction mixture was stirred at 140° C. overnight and then allowed to cool to room temperature. The reaction mixture was then filtered (1) and the filter was washed with 95,1 l of toluene (2). To the thus obtained organic phase, i.e. (1)+(2), was added 380,4 l of water and the mixture was stirred vigorously. Then agitation was stopped and the phases were separated (3). The water layer was washed once with 95,1 l of toluene and the phases were separated again (4). The combined organic phases, i.e. (3)+(4), were transferred to the second reactor and distilled under reduced pressure. 190,2 l of EtOH was added and the mixture was stirred at room temperature. A solution of HCl (6N) in 2-propanol (18,13 l) was added at room temperature and the reaction mixture was stirred overnight at room temperature, followed by filtration (*). The obtained solid was washed with 14,74 l of 2-propanol (**) and dried under reduced pressure at 50° C. Yield: 50-60% of the hydrochloric acid salt (1:1) of the intermediate of formula (II). Additional product (10-15%) was recuperated by distillation of the filtrate (*) and wash liquid (**) followed by filtration at room temperature.

EXAMPLE A3

Preparation of the Intermediate of Formula (III) Wherein $W_1$ Represents Chloro, Said Intermediate being Represented by Formula (III-a)

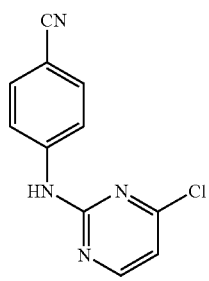

(III-a)

The intermediate of formula (III-a) was prepared based on the procedure as described in WO 99/50250.

In particular, a mixture of 4-[(1,4-dihydro-4-oxo-2-pyrimidinyl)amino]benzonitrile (0.12 mol) in POCl₃ (90 ml) was stirred and refluxed under Argon for 20 minutes. The reaction mixture was slowly poured onto 750 ml ice/water, and the solid was separated by filtration. The solid was suspended in 500 ml of water, and the pH of the suspension was adjusted to neutral by adding a 20% NaOH solution. The solid was again separated by filtration, suspended in 200 ml of 2-propanone, and 1000 ml of CH₂Cl₂ was added. The mixture was heated until all solid had dissolved. After cooling to room temperature, the aqueous layer was separated, and the organic layer was dried. During removal of the drying agent by filtration, a white solid formed in the filtrate. Further cooling of the filtrate in the freezer, followed by filtration, yielded 21.38 g (77.2%) of [4-[(4-chloro-2-pyrimidinyl)amino]benzonitrile, i.e. the intermediate of formula (III-a).

The retention time of intermediate (III-a) on Hypersil BDS (10 cm×4 mm×3 µm) eluted with 0.5% NH₄Ac/CH₃CN 90/10 at time 0 and 0/100 at 15 minutes was 8.33 minutes.

EXAMPLE A4

Preparation of the Intermediate of Formula (IV) Wherein $W_2$ is Bromo, Said Intermediate Being Represented by Formula (IV-a)

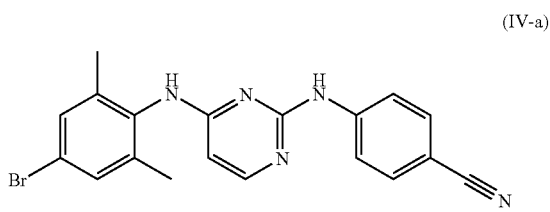

(IV-a)

A mixture of 4-bromo-2,6-dimethylbenzenamine (0.013 mol) and intermediate (III-a) (0.013 mol) was stirred at 150° C. for 1 hour. The mixture was poured into K₂CO₃ 10% aqueous solution and extracted with CH₂Cl₂/MeOH (95/5). The organic layer was separated, dried (MgSO₄), filtered and the solvent was evaporated. The residue was crystallized from diisopropyl ether. The precipitate was filtered off and dried. Yield: 2.3 g (45%). The mother layer was purified by column chromatography over silica gel (eluent: CH₂Cl₂/CH₃OH—NH₄OH 98/2/0.2; 15-40 µm). The pure fractions were collected and the solvent was evaporated. Yield: 0.90 g (17%). The global yield of intermediate (IV-a) was: 3.2 g (62%).

The retention time of intermediate (IV-a) on Hypersil BDS (10 cm×4 mm×3 µm) eluted with 0.5% NH₄Ac/CH₃CN 90/10 at time 0 and 0/100 at 15 minutes was 10.31 minutes.

Intermediate (IV), wherein $W_2$ represents iodo, said intermediate being represented by formula (IV-b), can be prepared on an analogous manner.

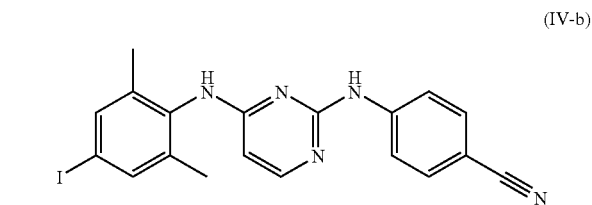

(IV-b)

The retention time of intermediate (IV-b) on Hypersil BDS (10 cm×4 mm×3 µm) eluted with 0.5% NH₄Ac/CH₃CN 90/10 at time 0 and 0/100 at 15 minutes was 10.54 minutes.

EXAMPLE A5 a) Preparation of Intermediate of Formula (VI) (E)

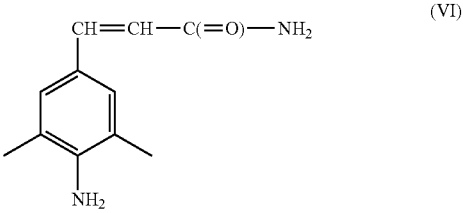

(VI)

In 10 ml acetonitrile, dry, was dissolved 2.00 g (10.0 mol) of 4-bromo-2,6-dimethylaniline, 1.07 g (1.5 eq) of acrylamide, 224 mg (0.1 eq) of Pd(OAc)$_2$, 609 mg (0.2 eq) of tris(2-methylphenyl)phosphine and 1.52 g of N,N-diethylethanamine. The mixture was purged with N$_2$ for 20 minutes and stirred overnight at 70° C. The mixture was diluted with 150 ml of methylene chloride, washed with sat. NaHCO$_3$ solution, dried (sat. NaCl, Na$_2$SO$_4$) and filtered. The solvent was evaporated and the residue was stirred in diisopropyl ether followed by filtration. Yield: 1.51 g (79.5%) of intermediate (VI) (E).

b) Preparation of Intermediate of Formula (II) (E)

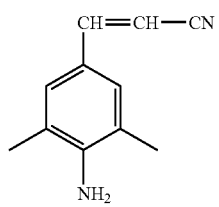

POCl$_3$ (3 ml) was cooled to 0° C. and 500 mg (2.63 mmol) of intermediate (VI) (E) was added. After 30 minutes, the cooling bath was removed and the mixture was stirred overnight at 20° C. The mixture was added dropwise to 150 ml of diisopropyl ether while stirring vigorously. The precipitate was filtered and washed with diisopropyl ether. The residue was added to 100 ml ethyl acetate/100 ml of saturated NaHCO$_3$ solution and stirred. The ethyl acetate layer was separated, dried (sat. NaCl, Na$_2$SO$_4$) and filtered. The solvent was evaporated. Yield: 380 mg (84%) of intermediate (II) (E).

c) Preparation of Intermediate of Formula (VII) (E)

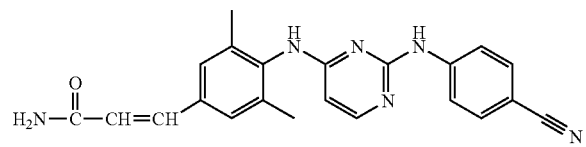

In a 100 ml flask under N$_2$ were introduced 0,8 g (4.33 mmol; 1 eq.) of intermediate (VI) (E), 1 g (4,33 mmol; 1 eq.) of intermediate (III-a) and 16 ml of 2-propanol. To this mixture 0,72 ml of HCl 6N in 2-propanol were added. The mixture was stirred under reflux for 72 hours and then cooled, yielding intermediate (VII) (E) HCl.

Intermediate (VII) (E) HCl can be converted into the free base according to art-known methodologies (see also Example B1). Intermediate of formula (VII) (E) can be converted into compound X according to the method described above in Example A5b.

EXAMPLE A6

Preparation of Intermediate of Formula (VII) (E)

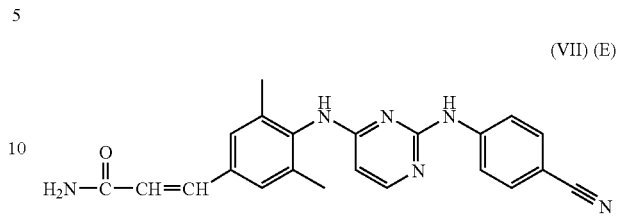

2.53 ml of acetonitrile, 0.056 g (0.253 mmol) of Pd(OAc)$_2$ and 0.154 g (0.506 mmol) of tris(2-methylphenyl)phosphine were brought in a 100 ml flask under nitrogen and the mixture was stirred for 10 minutes. To the mixture was added 1 g (2.53 mmol) of intermediate (IV-a), 0.51 ml (3.8 mmol) of N,N-diethylethanamine and 0.36 g (5.06 mmol) of acrylamide. The mixture was heated at reflux (80° C.) for 5 days yielding 28% of intermediate (VII) (E).

The retention time of intermediate (VII) (E) on Hypersil BDS (10 cm×4 mm×3 µm) eluted with 0.5% NH$_4$Ac/CH$_3$CN 90/10 at time 0 and 0/100 at 15 minutes was 6.59 minutes.

Intermediate of formula (VII) (E) can be converted into compound X according to the method described above in Example A5b.

B. Preparation of 4-[[4-[[4-(2-cyanoethenyl)-2,6-dimethylphenyl]amino]-2-pyrimidinyl]amino]benzonitrile (E) (Compound X) (Melting Point 245° C.)

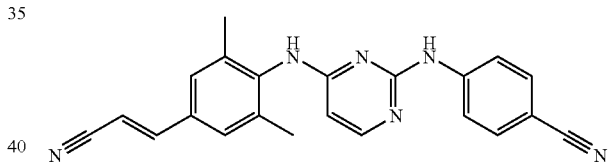

EXAMPLE B1 a) A mixture of 93.9 g (0.45 mol) of the hydrochloric acid salt of intermediate (II), prepared according to Example A2, and 109 g (0.4725 mol) of intermediate (III-a) in 1.8 l of acetonitrile was prepared under nitrogen atmosphere. The mixture was stirred and refluxed for 69 hours, then allowed to cool to 55° C. The mixture was filtered and the residue was washed with 200 ml of acetonitrile, followed by drying under reduced pressure at 50° C. overnight. 144,6 g (0.3666 mol) of the obtained solid was brought in 1 l of K$_2$CO$_3$ 10% aqueous solution. The mixture was stirred at room temperature followed by filtration. The obtained residue was washed twice with water followed by drying at 50° C. under reduced pressure. The residue was brought in 6.55 l isopropanol and the mixture was refluxed, then stirred overnight and filtered at room temperature. The residue was dried at 50° C. under reduced pressure. Yield: 113.2 g (68.6%) of 4-[[4-[[4-(2-cyanoethenyl)-2,6-dimethylphenyl]amino]-2-pyrimidinyl]amino]-benzonitrile (E) (Compound X).

b) A mixture of 93.9 g (0.45 mol) of the hydrochloric acid salt of intermediate (II), prepared according to Example A2, and 103.8 g (0.45 mol) of intermediate (III-a) in 0.9 l of acetonitrile was prepared under nitrogen atmosphere. The mixture was stirred and refluxed for 24 hours, then allowed to cool to 50° C. A solution of $K_2CO_3$ (124.4 g, 0.9 mol) in $H_2O$ (0.45 l) was added over a period of 15-20 minutes at 40-50° C., followed by stirring for 1 hour at 50° C. The precipitate was separated and washed twice with 0.045 l of acetonitrile, followed by drying at 50° C. under reduced pressure. 73.3 g of the obtained solid and 400 ml of EtOH were mixed and refluxed for 2 hours, then allowed to cool to room temperature. The precipitate was filtered and the residue was washed with 50 ml of EtOH. The obtained residue was dried overnight at 50° C. under reduced pressure. Yield: 65.7 g (89.6%) of 4-[[4-[[4-(2-cyanoethenyl)-2,6-dimethylphenyl]amino]-2-pyrimidinyl]amino]benzonitrile (E) (Compound X).

EXAMPLE B2

A mixture of intermediate (IV-a) (0.00021 mol), prepared according to Example A4, acrylonitrile ($CH_2=CH-CN$) (0.00213 mol), $Pd(OAc)_2$ (0.000043 mol), N,N-diethylethanamine (0.000043 mol) and tris(2-methylphenyl)phosphine (0.00021 mol) in $CH_3CN$ (7 ml) was stirred in a sealed vessel at 150° C. overnight. $H_2O$ was added. The mixture was extracted with $CH_2Cl_2$. The organic layer was separated, dried ($MgSO_4$), filtered and the solvent was evaporated. The residue (0.15 g) was purified by column chromatography over silica gel (eluent: $CH_2Cl_2$/ethyl acetate 80/20; 15-40 µm). Fraction 1 was collected and the solvent was evaporated, yielding 0.045 g of 4-[[4-[[4-(2-cyanoethenyl)-2,6-dimethylphenyl]amino]-2-pyrimidinyl]amino]benzonitrile (E/Z=80/20). The solid was crystallized from diethylether. Yield: 0.035 g of 4-[[4-[[4-(2-cyanoethenyl)-2,6-dimethylphenyl]amino]-2-pyrimidinyl]amino]benzonitrile (E) (Compound X) (55%).

EXAMPLE B3

4,41 g (10 mmol) of intermediate (IV-b) and 15 ml of N,N-dimethylacetamide were brought in a 100 ml flask under nitrogen. To this mixture were added 0,98 g of sodium acetate (12 mmol), 107 mg (0,1 mmol Pd) of Pd/C 10% (wet) and 1 ml (15 mmol) of acrylonitrile. The mixture was heated at 140° C. and the evolution of the reaction was followed by liquid chromatography. The reaction yielded 4-[[4-[[4-(2-cyanoethenyl)-2,6-dimethylphenyl]amino]-2-pyrimidinyl]amino] benzonitrile (E/Z=80/20) which can be worked up to yield 4-[[4-[[4-(2-cyanoethenyl)-2,6-dimethylphenyl]amino]-2-pyrimidinyl]amino]benzonitrile (E) as described above in Example B2.

The invention claimed is:

1. A process for the preparation of 4-[[4-[[4-(2-cyanoethenyl)-2,6-dimethylphenyl]amino]-2-pyrimidinyl]amino]benzonitrile of formula (I), a pharmaceutically acceptable acid addition salt, or a stereochemically isomeric form thereof (I)

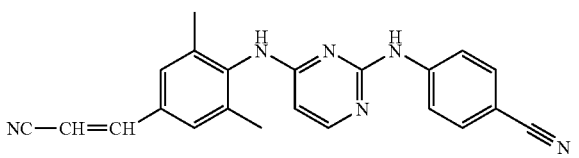

which comprises reacting an intermediate of formula (IV), or an appropriate acid addition salt thereof (IV)

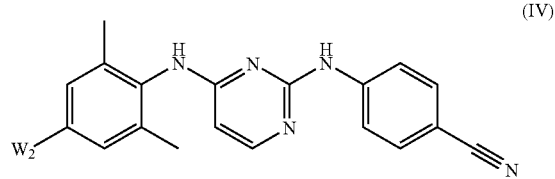

wherein $W_2$ represents a suitable leaving group, with acrylonitrile in the presence of a suitable palladium catalyst, a suitable base and a suitable solvent, optionally followed by converting the free base into an acid addition salt by treatment with an acid, or conversely, by converting the acid addition salt form into the free base by treatment with alkali; and optionally followed by preparing stereochemically isomeric forms thereof.

2. A process for the preparation of 4-[[4-[[4-(2-cyanoethenyl)-2,6-dimethylphenyl]amino]-2-pyrimidinyl]amino]benzonitrile of formula (I), pharmaceutically acceptable acid addition salt, or a stereochemically isomeric form thereof (I)

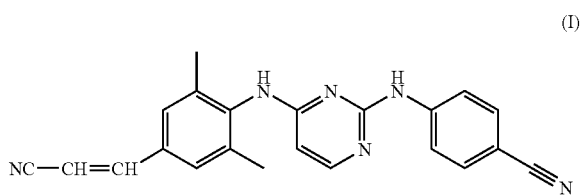

which comprises reacting an intermediate of formula (VI), an appropriate acid addition salt or a stereochemically isomeric form thereof (VI)

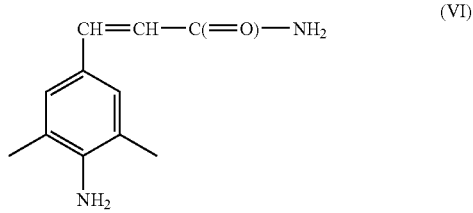

with an intermediate of formula (III) or an appropriate acid addition salt thereof (III)

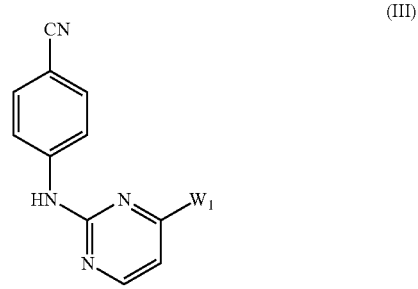

wherein $W_1$ represents a suitable leaving group, in the presence of a suitable solvent, followed by dehydration of the thus obtained intermediate of formula (VII), a pharmaceutically acceptable acid addition salt, a stereochemically isomeric form thereof,

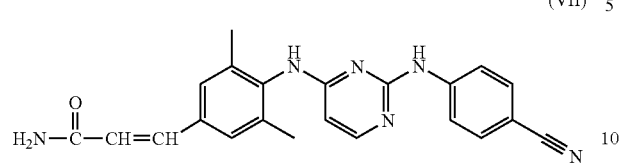
(VII)

optionally followed by converting the free base into an acid addition salt by treatment with an acid, or conversely, by converting the acid addition salt form into the free base by treatment with alkali; and optionally followed by preparing stereochemically isomeric forms thereof.

3. A process for the preparation of 4-[[4-[[4-(2-cyanoethenyl)-2,6-dimethylphenyl]amino]-2-pyrimidinyl]amino]benzonitrile of formula (I), a pharmaceutically acceptable acid addition salt, or a stereochemically isomeric form thereof

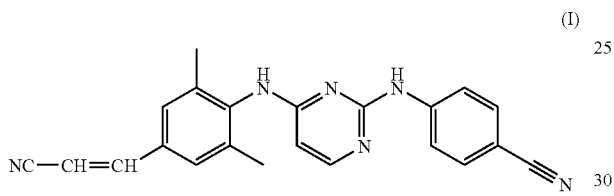
(I)

which comprises reacting an intermediate of formula (IV), or an appropriate acid addition salt thereof

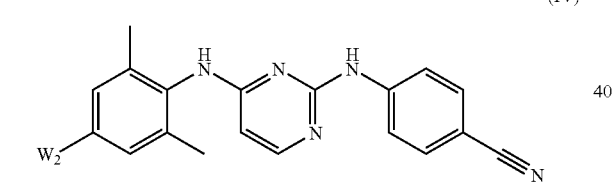
(IV)

wherein $W_2$ represents a suitable leaving group, with acrylamide in the presence of a suitable palladium catalyst, a suitable base and a suitable solvent,
followed by dehydration of the thus obtained intermediate of formula (VII), a pharmaceutically acceptable acid addition salt, or a stereochemically isomeric form thereof,

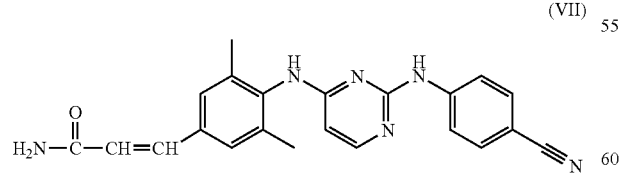
(VII)

optionally followed by converting the free base into an acid addition salt by treatment with an acid, or conversely, by converting the acid addition salt form into the free base by treatment with alkali; and optionally followed by preparing stereochemically isomeric forms thereof.

4. A process according to claim 1 wherein the palladium catalyst is a heterogeneous palladium catalyst.

5. A process according to claim 4 wherein the heterogeneous palladium catalyst is palladium on charcoal.

6. A process for the preparation of an intermediate of formula (II), an appropriate acid addition salt, or a stereochemically isomeric form thereof

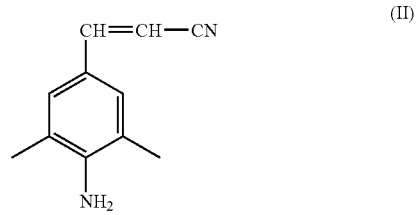
(II)

which comprises reacting an intermediate of formula (V) or an acid addition salt thereof,

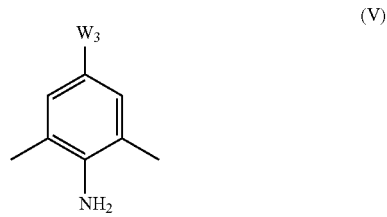
(V)

wherein $W_3$ represents a suitable leaving group, with acrylamide in the presence of a suitable palladium catalyst, a suitable base and a suitable solvent,
followed by dehydration of the thus obtained intermediate of formula (VI), an appropriate acid addition salt, or a stereochemically isomeric form thereof,

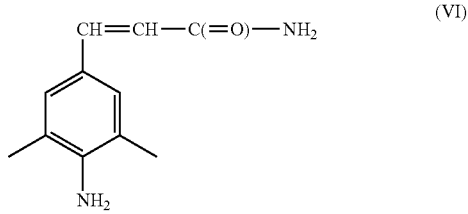
(VI)

optionally followed by converting the free base into an acid addition salt by treatment with an acid, or conversely, by converting the acid addition salt form into the free base by treatment with alkali; and optionally followed by preparing stereochemically isomeric forms thereof.

7. A process according to claim 1 wherein [[4-[[4-(2-cyanoethenyl)-2,6-dimethylphenyl]amino]-2-pyrimidinyl]amino]benzonitrile (E) or a pharmaceutically acceptable acid addition salt thereof is prepared.

8. A process according to claim 2 wherein 4-[[4-[[4-(2-cyanoethenyl)-2,6-dimethylphenyl]amino]-2-pyrimidinyl]amino]benzonitrile (E) or a pharmaceutically acceptable acid addition salt thereof is prepared.

9. A process according to claim 3 wherein 4-[[4-[[4-(2-cyanoethenyl)-2,6-dimethylphenyl]amino]-2-pyrimidinyl]amino]benzonitrile (E) or a pharmaceutically acceptable acid addition salt thereof is prepared.

* * * * *